US011497930B2

(12) United States Patent
Powell (10) Patent No.: US 11,497,930 B2
(45) Date of Patent: Nov. 15, 2022

(54) PHOTOTHERAPY DEVICE AND SYSTEM (71) Applicant: Patrick Kenneth Powell, Detroit, MI (US)

(72) Inventor: Patrick Kenneth Powell, Detroit, MI (US)

(73) Assignee: AG IP HOLDING LLC, Troy, MI (US)

(*) Notice: Subject to any disclaimer, the term of this patent is extended or adjusted under 35 U.S.C. 154(b) by 0 days.

(21) Appl. No.: 16/696,197

(22) Filed: Nov. 26, 2019

(65) Prior Publication Data
US 2020/0164221 A1 May 28, 2020

Related U.S. Application Data (60) Provisional application No. 62/772,340, filed on Nov. 28, 2018, provisional application No. 62/772,317, filed on Nov. 28, 2018, provisional application No. 62/772,337, filed on Nov. 28, 2018.

(51) Int. Cl.
A61N 5/06 (2006.01)

(52) U.S. Cl.
CPC .... A61N 5/0621 (2013.01); A61N 2005/0638 (2013.01); A61N 2005/0661 (2013.01); A61N 2005/0662 (2013.01); A61N 2005/0666 (2013.01)

(58) Field of Classification Search
CPC .......................................................... A61F 7/08
See application file for complete search history.

(56) References Cited

U.S. PATENT DOCUMENTS

| 3,877,437 | A |   | 4/1975  | Maitan et al. |
|-----------|---|---|---------|---------------|
| 5,824,023 | A | * | 10/1998 | Anderson ............ A61B 18/203 607/88 |
| 6,045,575 | A |   | 4/2000  | Rosen et al. |
| 6,464,715 | B1|   | 10/2002 | Gysens et al. |
| 6,596,016 | B1|   | 7/2003  | Vreman et al. |
| 6,811,563 | B2|   | 11/2004 | Savage, Jr. et al. |
| 6,872,220 | B2|   | 3/2005  | Williams et al. |
| 7,147,653 | B2|   | 12/2006 | Williams et al. |
| 9,227,082 | B2|   | 1/2016  | McDaniel |

(Continued)

FOREIGN PATENT DOCUMENTS

| DE | 3910238    | 3/1990  |
|----|------------|---------|
| FR | 2648036    | 12/1990 |
| WO | 2017004257 | 1/2017  |

OTHER PUBLICATIONS

Shi, He & Liu, Hongbin & Ni, Yonghao & Yuan, Z. & Zou, Xuejun & Zhou, Yajun. (2012). Review: Use of optical brightening agents (OBAs) in the production of paper containing high-yield pulps. BioResources. 7. 10.15376/biores.7.2.2582-2591. (Year: 2012).*

Primary Examiner — Michael W Kahelin
Assistant Examiner — Michael A Rizzuto
(74) Attorney, Agent, or Firm — Carlson, Gaskey & Olds, P.C.

(57) ABSTRACT

A ring has an open top side and side walls that circumscribe a central region for receiving a phototherapy subject. The side walls include a work surface that is configured to receive visible light through the open top side and reflect the visible light toward the central region for phototherapy. The work surface includes a first surface that is a diffuse reflector and a second surface that is a specular reflector.

20 Claims, 11 Drawing Sheets (56) References Cited

U.S. PATENT DOCUMENTS

| | | |
|---|---|---|
| 9,385,337 B2 | 7/2016 | Pan |
| 9,604,072 B2 | 3/2017 | Brezinski |
| 10,286,226 B2 | 5/2019 | Chakravarthy et al. |
| 10,369,377 B2 * | 8/2019 | Palaniswamy ............ A61F 7/08 |
| 2002/0035386 A1 * | 3/2002 | Whitehurst ............ A61N 5/062 |
| | | 607/88 |
| 2003/0147241 A1 * | 8/2003 | Hildebrand ........... F21V 33/004 |
| | | 362/231 |
| 2004/0039428 A1 | 2/2004 | Williams et al. |
| 2007/0032842 A1 | 2/2007 | Strong |
| 2007/0188425 A1 * | 8/2007 | Saccomanno .......... H05B 45/48 |
| | | 345/82 |
| 2007/0208397 A1 | 9/2007 | Gardner |
| 2008/0269844 A1 | 10/2008 | Logslett |
| 2009/0018622 A1 | 1/2009 | Asvadi et al. |
| 2010/0179469 A1 | 7/2010 | Hammond et al. |
| 2012/0253433 A1 | 10/2012 | Rosen et al. |
| 2013/0044476 A1 * | 2/2013 | Bretschneider ......... F21V 29/70 |
| | | 362/235 |
| 2013/0226268 A1 | 8/2013 | Pan |
| 2014/0031906 A1 | 1/2014 | Brezinski |
| 2016/0263396 A1 | 9/2016 | Chajravarthy et al. |
| 2017/0312542 A1 | 11/2017 | Palaniswamy et al. |
| 2018/0177434 A1 | 6/2018 | Kim et al. |
| 2018/0185665 A1 | 7/2018 | Osterhout et al. |
| 2018/0207446 A1 | 7/2018 | Jones |
| 2018/0361171 A1 | 12/2018 | Powell |
| 2019/0099613 A1 | 4/2019 | Estes et al. |
| 2019/0099616 A1 | 4/2019 | Kavoori Sethumadhavan et al. |
| 2019/0224496 A1 | 7/2019 | Van Abeelen et al. |
| 2019/0232082 A1 | 8/2019 | Palaniswamy et al. |
| 2020/0038679 A1 * | 2/2020 | Brezinski ............. A61N 5/0621 |

* cited by examiner

PHOTOTHERAPY DEVICE AND SYSTEM

CROSS REFERENCE TO RELATED APPLICATION

This application claims priority to U.S. Provisional Application Nos. 62/772,317; 62/772,337; and 62/772,340, all filed on Nov. 28, 2018.

BACKGROUND

In the field of pediatric jaundice treatment, the primary therapy is to irradiate exposed skin of the newborn baby with visible blue or green light. The light causes a photochemical reaction of unconjugated bilirubin into an isomer that is more easily processed out of the body.

SUMMARY

A phototherapy device according to an example of the present disclosure includes a ring having an open top side and side walls that circumscribe a central region for receiving a phototherapy subject. The side walls have a work surface that is configured to receive visible light through the open top side and reflect the visible light toward the central region for phototherapy. The work surface has a first surface that is a diffuse reflector and a second surface that is a specular reflector.

In a further embodiment of any of the foregoing embodiments, the ring includes a front and a back, and the diffuse reflector is on the back and the specular reflector is on the front.

In a further embodiment of any of the foregoing embodiments, the specular reflector or the diffuse reflector makes up at least 15% of the surface area of the work surface, and the other of the specular reflector or the diffuse reflector makes up a remainder of the surface area of the work surface.

In a further embodiment of any of the foregoing embodiments, the specular reflector or the diffuse reflector makes up at least 40% of the surface area of the work surface, and the other of the specular reflector or the diffuse reflector makes up a remainder of the surface area of the work surface.

In a further embodiment of any of the foregoing embodiments, the ring has a racetrack oval shape and the side walls include two opposed elongated walls that extend approximately parallel to a longitudinal axis.

In a further embodiment of any of the foregoing embodiments, the specular reflector is on one of two opposed elongated walls and the diffuse reflector is on the other of the two opposed elongated walls.

In a further embodiment of any of the foregoing embodiments, the diffuse reflector is a Lambertian reflector.

In a further embodiment of any of the foregoing embodiments, the diffuse reflector has a TAPPI brightness of 70 to 130, and the specular reflector has a reflectance of at least 70% based on a quotient of radiance reflected and radiance received.

In a further embodiment of any of the foregoing embodiments, the diffuse reflector includes one or more additives that are operable to convert ultraviolet radiation that is received through the open top side into visible light.

In a further embodiment of any of the foregoing embodiments, the first surface has ridges. Each of the ridge includes a portion that is sloped relative to vertical toward a bottom of the ring.

In a further embodiment of any of the foregoing embodiments, the bottom is reflective.

In a further embodiment of any of the foregoing embodiments, the specular reflector includes a straight reflector portion and a parabolic reflector portion.

In a further embodiment of any of the foregoing embodiments, a portion of the side wall that has the specular reflector has a height H1 taken from a horizontal plane of a bottom of the ring and another portion of the side wall that has the diffuse reflector has a height H2 taken from the horizontal plane, and the height H1 is 20% to 80% of the height H2.

In a further embodiment of any of the foregoing embodiments, the ring includes a bottom, and the bottom has a release door.

In a further embodiment of any of the foregoing embodiments, the release door includes a panel and a hinge.

In a further embodiment of any of the foregoing embodiments, the release door includes a panel and an elastic retainer.

In a further embodiment of any of the foregoing embodiments, the ring has a fitted shape with respect to human body shape.

A further embodiment of any of the foregoing embodiments includes a head alignment structure that defines an interior head pocket and vents.

A phototherapy system according to an example of the present disclosure includes a light source operable to emit visible light, and a ring vertically below the light source. The ring has an open top side and side walls that circumscribe a central region for receiving a phototherapy subject. The side walls have a work surface that is configured to receive the visible light through the open top side and reflect the visible light toward the central region for phototherapy. The work surface includes a first surface that is a diffuse reflector and a second surface that is a specular reflector.

In a further embodiment of any of the foregoing embodiments, the ring includes a front and a back, the light source obstructs the back, the diffuse reflector is on the back, and the specular reflector is on the front.

BRIEF DESCRIPTION OF THE DRAWINGS

The various features and advantages of the present disclosure will become apparent to those skilled in the art from the following detailed description. The drawings that accompany the detailed description can be briefly described as follows.

DETAILED DESCRIPTION

Figure 1A:
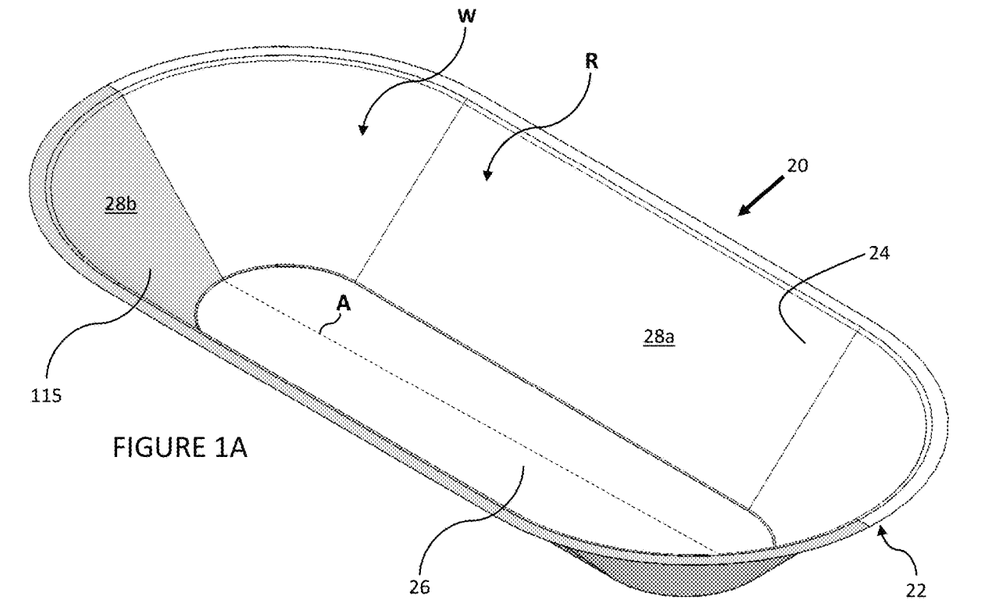
FIG. 1A illustrates an isometric view of a phototherapy device.
Figure 1B:
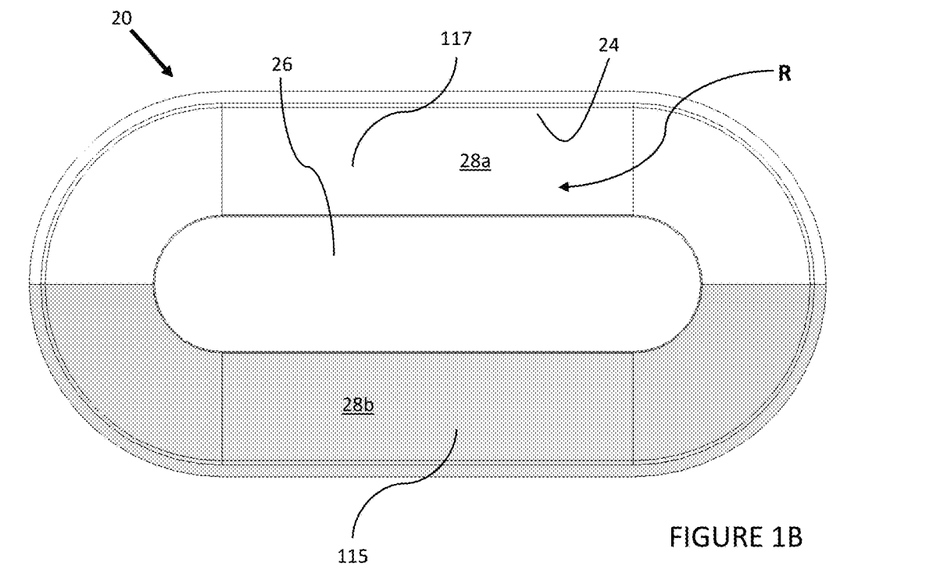
FIG. 1B illustrates a planar view of the device of FIG. 1A.

FIGS. 1A and 1B schematically illustrate an example phototherapy device 20. The phototherapy device 20 may be used for pediatric jaundice treatment. It is to be understood, however, that although the examples herein may be described and shown with regard to jaundice phototherapy, the device 20 may also find benefit in other end uses.

As shown, the phototherapy device 20 is in the form of a ring 22 that is formed by one or more side walls 24 that circumscribe a central region R for receiving a phototherapy subject, such as a baby. In this example, the ring 22 has a racetrack oval shape with two opposed elongated walls that extend approximately parallel to a longitudinal axis A. Opposed curved end walls join the side walls. A bottom 26 of the ring 22 may be open or may be a solid wall, and the top of the ring 22 is open. In general, the bottom 26 is associated with or defines a horizontal plane, while the direction orthogonal is vertical. The shape here is useful for jaundice treatment in that the region R is generally suitable for accommodating a baby. It is to be appreciated that the shape may be varied somewhat, but most typically will be oval or an oval variation.

The side walls 24 define a work surface W that generally faces into the region R and is configured to reflect radiation received through the open top of the ring 22, mainly visible light but also at least a portion of the ultraviolet band of the spectrum. The work surface W is the surface (or surfaces) of the device 20 that is functionalized for directed reflectance toward the region R and, in particular, toward a focal portion of the region R in which the phototherapy subject is to reside for therapeutic purposes. In this regard, the work surface or surfaces W will have the characteristics of a) being functionalized for a specific type of reflectance, such as with an engineered surface that is designed to provide a particular type of reflectance, and b) being oriented to direct reflected light toward the focal portion, such as with a slope or curvature that is oriented toward the focal portion. In this regard, the work surface or surfaces W are configured for the main purpose of directing light at the focal portion for therapeutic purposes, while surfaces that are on ancillary components that primarily serve other purposes and that only incidentally reflect light are not considered working surfaces.

For jaundice, the visible light of interest is blue and green light (400-550 nm wavelength). In that regard, the work surfaces W are sloped and reflective. However, the surfaces are configured to have different reflectance. For example, the work surface W includes a surface 28a is a diffuse reflector and a surface 28b that is a specular reflector. In the figure, the surfaces 28a/28b are shaded differently to demonstrate the extent of each. The different types of reflectance surfaces facilitate tailoring the performance of the phototherapy device 20 with regard to therapeutic effectiveness and ergonomics, for example. In further examples, at least 15% of the surface area of the work surface and up to about 85% is made up of the surface 28b, with the remaining surface area being made up of the surface 28a, excluding any gaps, joints, or the like (i.e., non-work surfaces). In further examples, each of the surfaces 28a/28 will make up at least 30% or at least 40% of the surface area that bounds region R, excluding any gaps, joints, or the like. In the example shown, the surface area containing the surface 28a is continuous and the surface area containing the surface 28b is continuous. It is to be appreciated, however, that the surfaces 28a and/or 28b may alternatively be discontinuous, such as with a plurality of discrete sections of surface 28a and/or 28b.

A specular reflector reflects each incident ray at the same angle to the surface normal as the incident ray, but on the opposing side of the surface normal in the plane formed by incident and reflected rays. A diffuse reflector reflects a ray but scatters it at many angles rather than at just one angle as for the specular reflector. One example diffuse reflector for the surface 28a is a Lambertian reflector that reflects light with equal luminance when viewed from all directions lying in the half-space adjacent to the surface. For instance, the reflectance of the surface 28a follows Lambert's cosine law in which the radiant intensity or luminous intensity observed from an ideal diffusely reflecting surface is directly proportional to the cosine of the angle θ between the direction of the incident light and the surface normal. For example, the surfaces 28a may be provided by papers, foils, paints, or similar materials that provide the diffuse reflection.

In a further example, the surface 28a is a Lambertian reflector with a high brightness. For instance the surface 28a has a TAPPI brightness of 70 to 130. In additional examples, the paper, foil, paint, or other material of the surface 28a includes one or more additives or pigments for enhancing performance, such as optical brightening agents or fluorescing agents. An optical brightening agent is a chemical compound that absorbs ultraviolet and violet radiation (typically 180-400 nm) and re-emits visible light in the blue range (e.g., 400-520 nm). Example optical brightening agents may include, but are not limited to, di-, tetra-, and hexa-sulfonated agents of stilbene derivatives (e.g., diphenylethene). Further example agents are 4,4'-diamino-2,2'-stilbenedisulfonic acid, 4,4'-bis(benzoxazolyl)-cis-stilbene, and 2,5-bis(benzoxazol-2-yl)thiophene. The conversion increases brightness, as radiation that was non-visible radiation becomes visible. Such conversion may also facilitate increasing energy efficiency, as additional radiation from a light source can be used for therapy. Such conversion may also serve to limit the negative biological effects of UV irradiation transfer to the patient.

Example specular reflectors for the surface 28b are mirrored or polished surfaces. In general, the specular reflector has a reflectance of at least 50% based on the quotient of radiance reflected and the radiance received. In further examples, the reflectance is at least 70% to as high as 100% for enhanced therapeutic effect. For example, the surface 28b may be provided by papers, foils, paints, or similar materials that provide the specular reflectance.

When used for phototherapy, an overhead light source is provided vertically above the phototherapy device 20. In this regard, the phototherapy device 20 and the light source may be considered to be part of a phototherapy system for treating a phototherapy subject, such as a baby. The light impinges the surfaces 28a/28b. Due to the sloped angle of the side walls 24, the ring 22 generally directs the light toward the region R. Thus, the ring 22 redirects light that does not directly impinge on a baby in the region R, thereby increasing the irradiance on the baby.

The different reflectance of the surfaces 28a/28b facilitates tailoring the performance of the phototherapy device 20. For instance, the specular reflectance of the surface 28b provides highly efficient redirection of the light toward the region R, and the diffuse reflectance of the surface 28a provides less efficient redirection of the light toward the region R. Although highly efficient, the specular reflectance of the surface 28b provides a relatively intense visual effect, e.g., high glare. For instance, the specular reflectance of the surface 28b can reflect high intensity light from the light source and/or other surrounding objects directly at the eyes of a user, such as a doctor or nurse. The diffuse reflectance of the surface 28a is less efficient but provides a relatively less intense visual effect, e.g., a lower glare. For instance, due to light diffusion, the light reflected at the user is less intense. Thus, the sizes and positioning of the surfaces 28a/28b are configured to provide good light redirection, yet reduce visual intensity for the user.

For example, the phototherapy device 20 generally has a front and a back. The front is the side from which the user approaches and uses the phototherapy device 20, such as to insert and remove a baby from the phototherapy device 20. The back is the side opposite the front. In general, in practical use, user-access to the back is likely to be limited or obstructed by additional equipment, such as a lamp. In the example shown, the side wall 24 that has the surface 28b is the front and the side wall 24 that has the surface 28a is the back. For instance, the back excludes any specular reflectors. Assuming the eye level of the user is vertically above the phototherapy device 20, on approach and during use a greater amount of the area of the surface 28a is in line-of-view of the user than area for the surface 28b. As a result, the user is exposed mainly to the lower visual intensity area of the surface 28a rather than the higher visual intensity area of the surface 28b. Yet, an increased amount of light impinges the baby in the region R due to the higher efficiency of the reflectance of the surface 28b. Moreover, although the surface 28a is a diffuse reflector, at least a portion of the light reflected from the surface 28b also impinges on the baby in region R. Thus, the surface 28b reduces visual intensity but still provides some therapeutic effect. The phototherapy device 20 therefore provides a user-friendly experience but maintains a high level of therapeutic effectiveness.

Figure 2A:
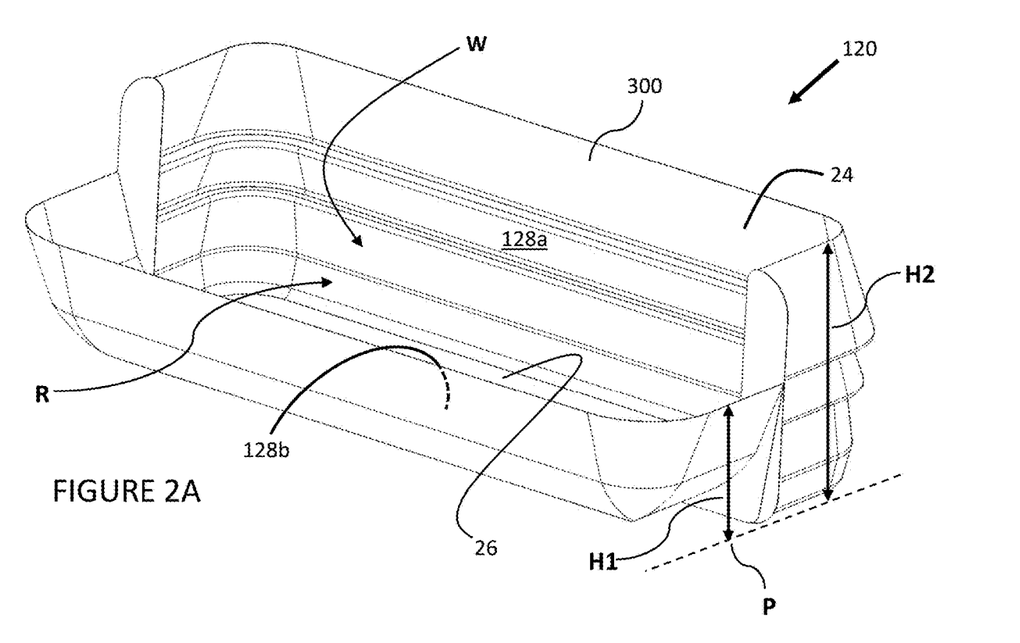
FIG. 2A illustrates an isometric view from the front side of another example phototherapy device.
Figure 2B:
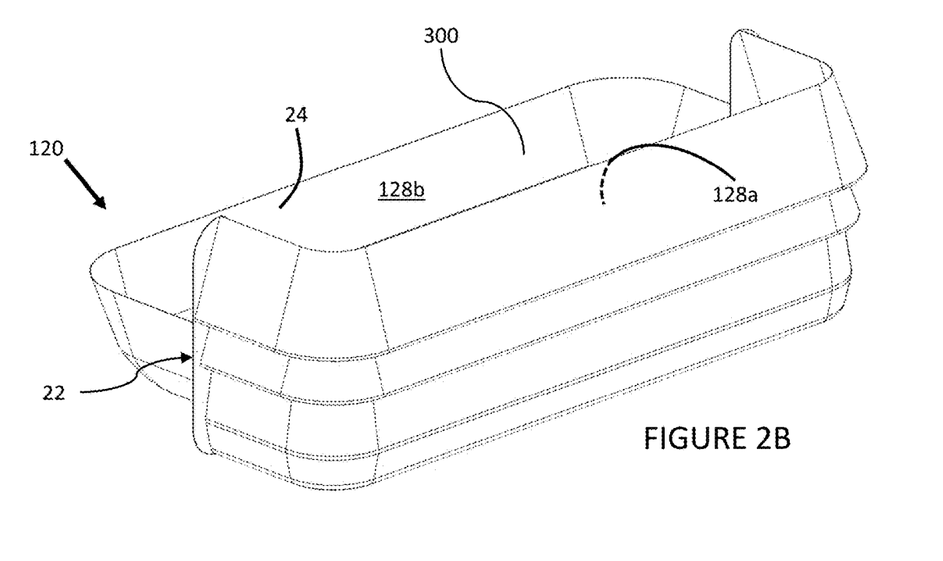
FIG. 2B illustrates an isometric view of from the back side of the device of FIG. 2A.
Figure 3:
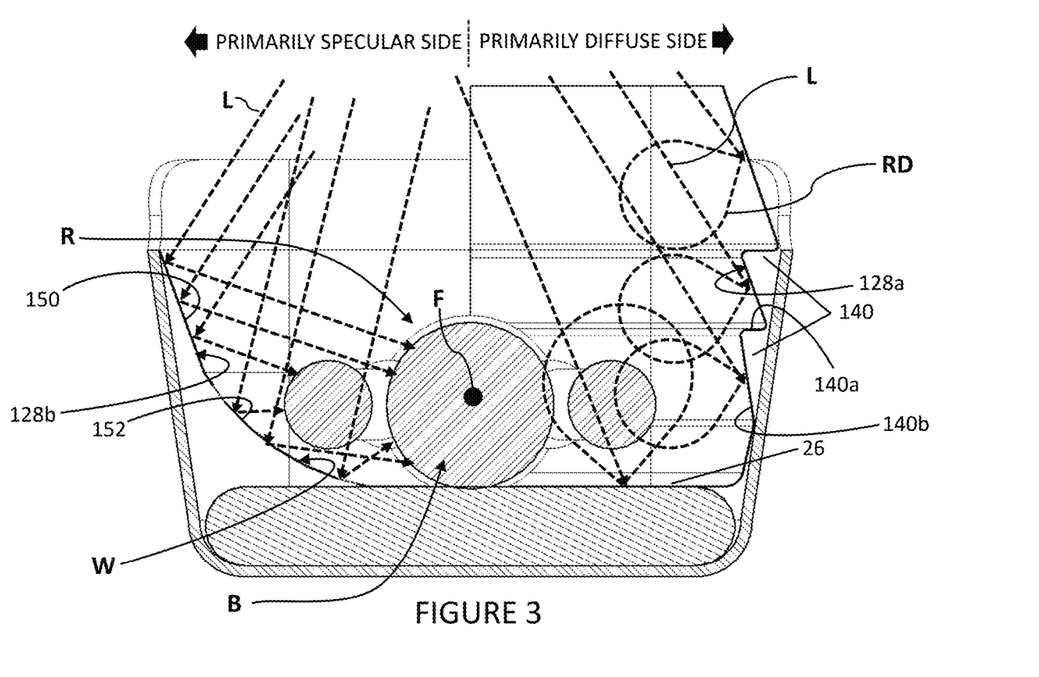
FIG. 3 illustrates a sectioned view of the device of FIGS. 2A/2B showing light reflection.
Figure 4A:
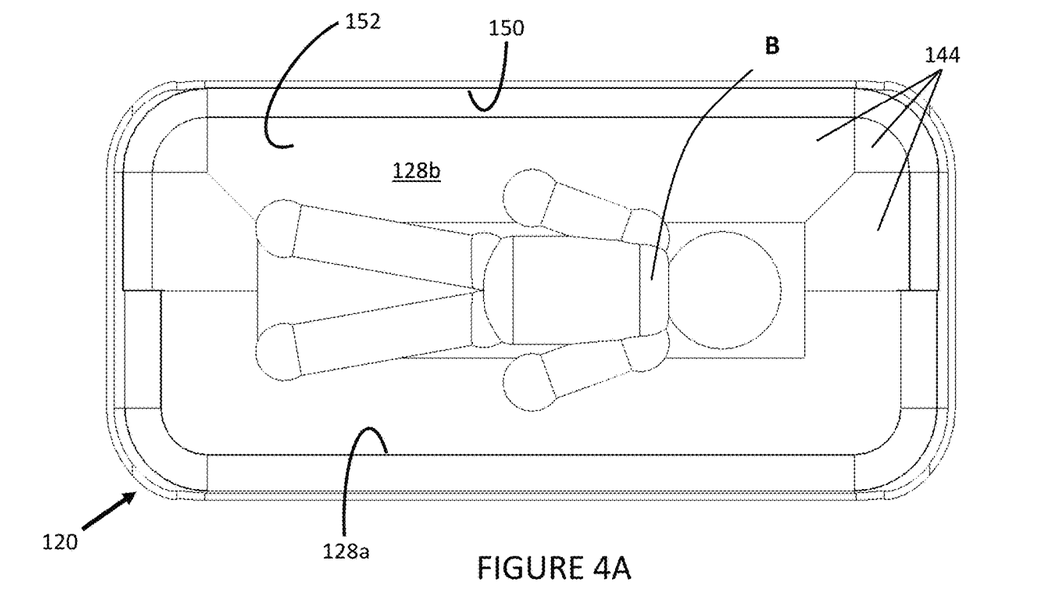
FIG. 4A illustrates an overhead view of the device of FIG. 2A/2B with a phototherapy subject.
Figure 4B:
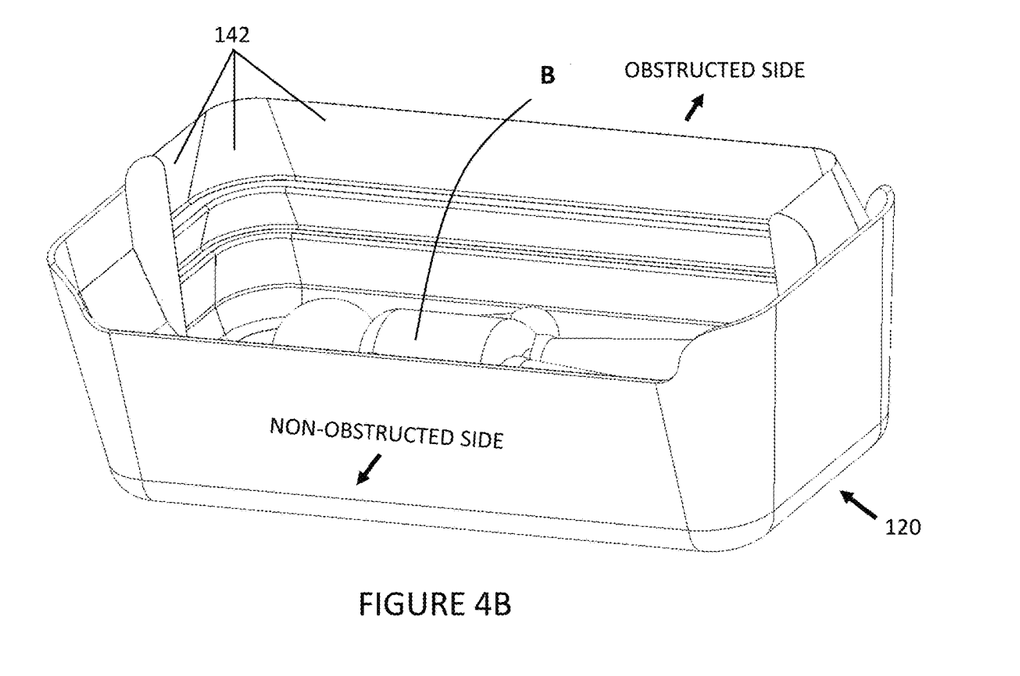
FIG. 4B illustrates an isometric view of the device of FIG. 2A/2B with a phototherapy subject.

FIGS. 2A and 2B illustrate another example of a phototherapy device 120; FIG. 3 illustrates a sectioned view of the phototherapy device 120; and FIGS. 4A and 4B illustrate additional views of the phototherapy device 120 with a baby. In this disclosure, like reference numerals designate like elements where appropriate and reference numerals with the addition of one-hundred or multiples thereof designate modified elements that are understood to incorporate the same features and benefits of the corresponding elements. In this example, similar to the phototherapy device 20, the surface 128a is a diffuse reflector and the surface 128b is a specular reflector. However, each of the surfaces 128a/128b are further configured to enhance effectiveness.

The surface 128a includes ridges 140. Each ridge 140 defines a first, or upper, surface portion 140a and a second, or lower, surface portion 140b. The upper surface portion 140a is generally horizontal but may be varied. The lower surface portion 140b is sloped, relative to the vertical direction, toward to the bottom 26 of the phototherapy device 120. The surface 128a may be provided as a continuous surface or wall but more typically will be provided in sections or pieces that are attached together. For instance, the surface 128a is made up of end sections, corner sections, and side sections, all generally designated at 142 (FIG. 4B).

In use, incoming light L impinges on the lower surfaces 140b and diffusively reflects, as represented at RD. At least a portion of the diffusively reflected light RD impinges a baby, represented at B, in the region R. Other portions of the diffusively reflected light RD may be above or below the baby B. In this example, the bottom 26 is reflective such that the portion of the diffusively reflected light RD that is below the baby is reflected from the bottom 26 toward the baby B. The ridges 140 and the reflective bottom 26 thus facilitate enhanced effectiveness by directing light toward the baby B that may otherwise be lost.

The surface 128b is a compound reflective surface. In this example, an upper portion 150 of the surface 128b is straight and a lower portion 152 of the surface 128b is parabolic. Similar to the surface 128a, the surface 128b is made up of end sections, corner sections, and side sections, all generally designated at 144 (FIG. 4A). As an example, the corner section is a radial reflector that has a radius of greater than zero.

In use, the straight portion 150 reflects incoming light L downwards toward the baby B, generally onto the upper portion of the baby B. The parabolic portion 152 reflects light sideways, toward one or more focal points F that generally coincide with the position of the baby B, onto the lower portion of the baby B.

An additional aspect of the phototherapy device 120 relates to the configuration of the side wall 24. In general, entirely short side walls may result in relatively high light loss but permit relatively unobstructed user access and sight lines to a baby B. Entirely tall side walls contain more light for therapeutic use but may obstruct user access and sight lines to the baby B. In this regard, the phototherapy device 120 facilitates relatively free access and sight lines while also containing light. Referring to FIG. 2A, the portion of the side wall 24 that has the surface 128b, i.e., the front, is shorter in height than the portion of the side wall 24 that has the surface 128a, i.e., the back. The shorter front permits ready access and sight lines, while the taller back facilitates containing light. For instance, from a horizontal plane P of the bottom 26, a height H1 of the side with the surface 128b is shorter than a height H2 of the side with the surface 128a. As a further example, the top of the side with the surface 128b is 20% to 80% below the top of the side that has the surface 128a. In an additional example, the top of the side with the surface 128b is 25% to 50% below the top of the side that has the surface 128a. In yet a further example, a useful height H2 for the purposes above is from 3 inches to 12 inches.

Figures 5A, 5B:
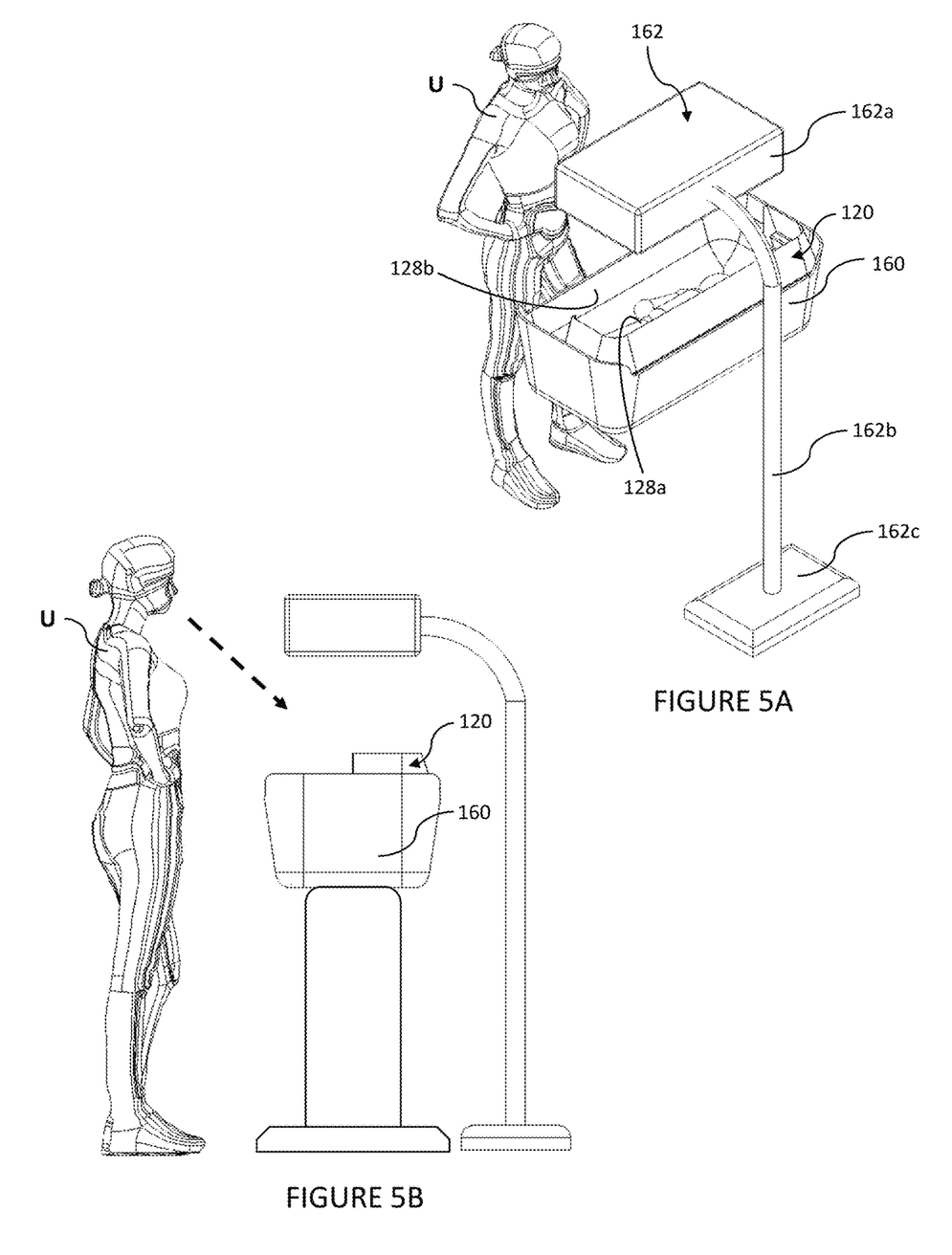
FIG. 5A illustrates an isometric view of the device of FIG. 2A/2B with a light source in a phototherapy system.
FIG. 5B illustrates a side view of the phototherapy system of FIG. 5A.

FIGS. 5A and 5B demonstrate an example of the phototherapy device 120 in an end use environment with a user, designated at U. In the illustrated configuration the phototherapy device 120 is in a bassinet 160 that is supported on a stand. An overhead light source 162 is suspended vertically over the bassinet 160 and phototherapy device 120. In the example shown, the light source 162 includes a light 162a, a support arm 162b, and a base 162c. The support arm 162b and base 162c obstruct one side of the bassinet 160 and phototherapy device 120. For example, the support arm 162*b* and base 162*c* limit walk-up access by a user to one side of the phototherapy device 120. The user is thus unlikely to or unable to approach from the obstructed side and thus approaches or uses the phototherapy device 120 from the side opposite the arm 162*b* and base 162*c*. In such an arrangement in which one side is obstructed, the specular reflectance surface 128*b* faces toward the obstructed side and the diffuse reflectance surface 128*a* faces toward the non-obstructed side. Put another way, the side wall 24 that has the surface 128*a* (the back) is on the obstructed side and the side wall that has the surface 128*b* (the front) is on the user side. The surface 128*b* thus reflects light in a direction away from the non-obstructed user side, while the surface 128*a* that provides relatively lower glare to the non-obstructed user side. The obstructed and non-obstructed sides are also designated in FIG. 4B.

Figure 6A:
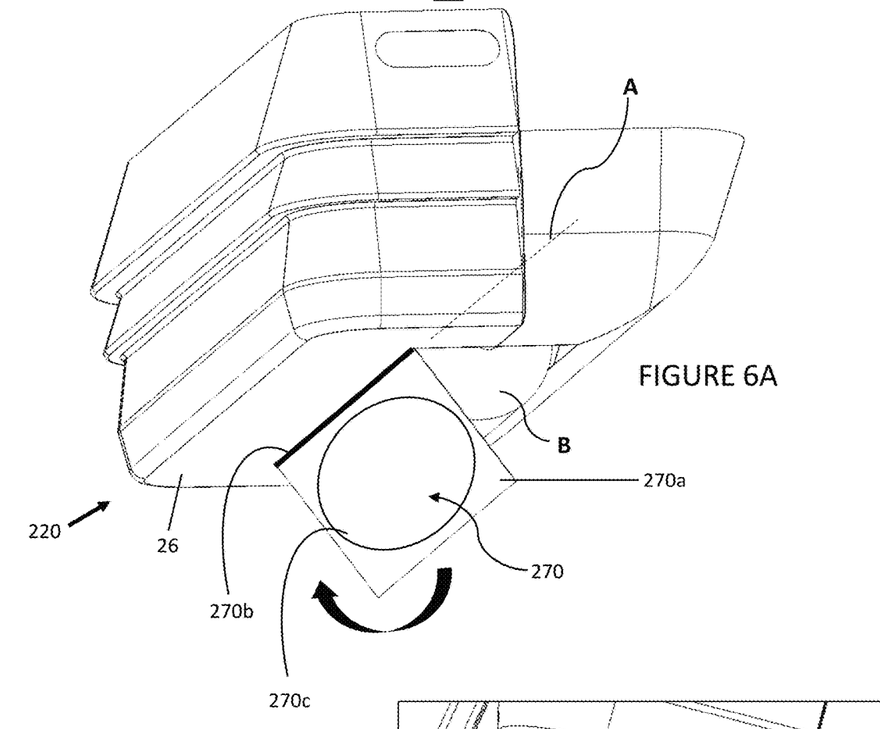
FIG. 6A illustrates an isometric view of another example phototherapy device with a release door (trap door).
Figure 6B:
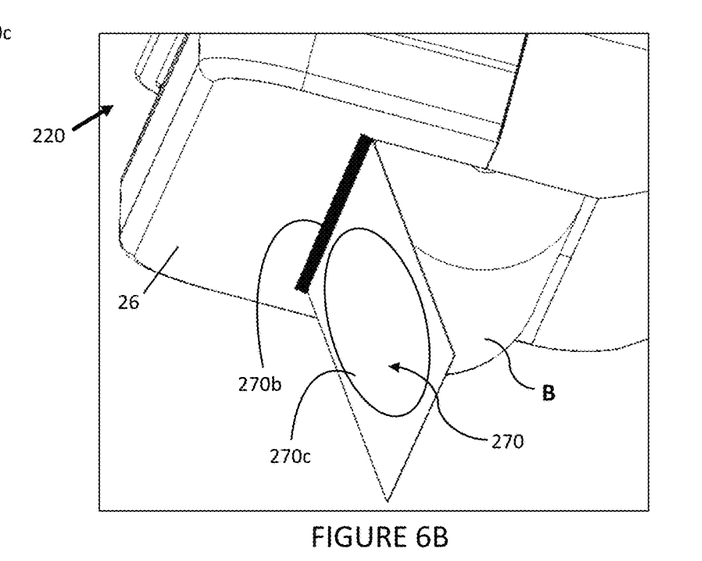
FIG. 6B illustrates the release door (trap door) in operation.

FIGS. 6A and 6B illustrate another example phototherapy device 220. The phototherapy device 220 is the same as the phototherapy device 120 except that the bottom 26 includes a release door 270. In this example, the release door 270 is a trap door that includes a panel 270*a* and a hinge 270*b* that is pivotable along an axis that is parallel or substantially parallel to the longitudinal axis A of the phototherapy device 220.

The release door 270 is configured to facilitate the prevention of the phototherapy device 220 from being used as a carrier. For instance, in the event that the phototherapy device 220 is picked up with the baby B in it, the panel 270*a* gives way under the weight of the baby B such that the panel 270*a* pivots about the hinge 270*b*. The weight of a baby may vary, but in general the weight under which the release door 270 releases is about one pound or more. The baby B can thus remain in a substantially unmoved position by moving through the release door 270 as the phototherapy device 220 is lifted upwards around the baby B.

In a further example, the panel 270*a* is formed of or includes a disposable absorbent layer 270*c*. The absorbent layer 270*c* serves to absorb fluids and may also be soft to provide comfort.

In additional examples, the hinge 270*b* is an adhesive, such as an adhesive tape, that attaches the panel 270*a* to the bottom 26. The adhesive is pliable under the weight of a baby B such that it acts as a hinge when the phototherapy device 220 is lifted.

Figure 7A:
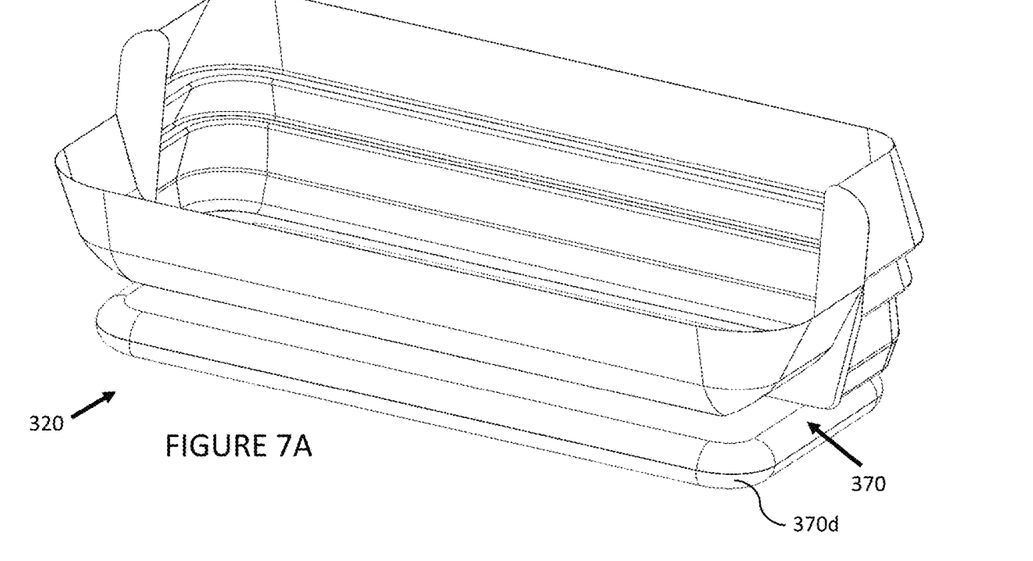
FIG. 7A illustrates an isometric view of another example phototherapy device with a release door (panel/retainer).
Figure 7B:
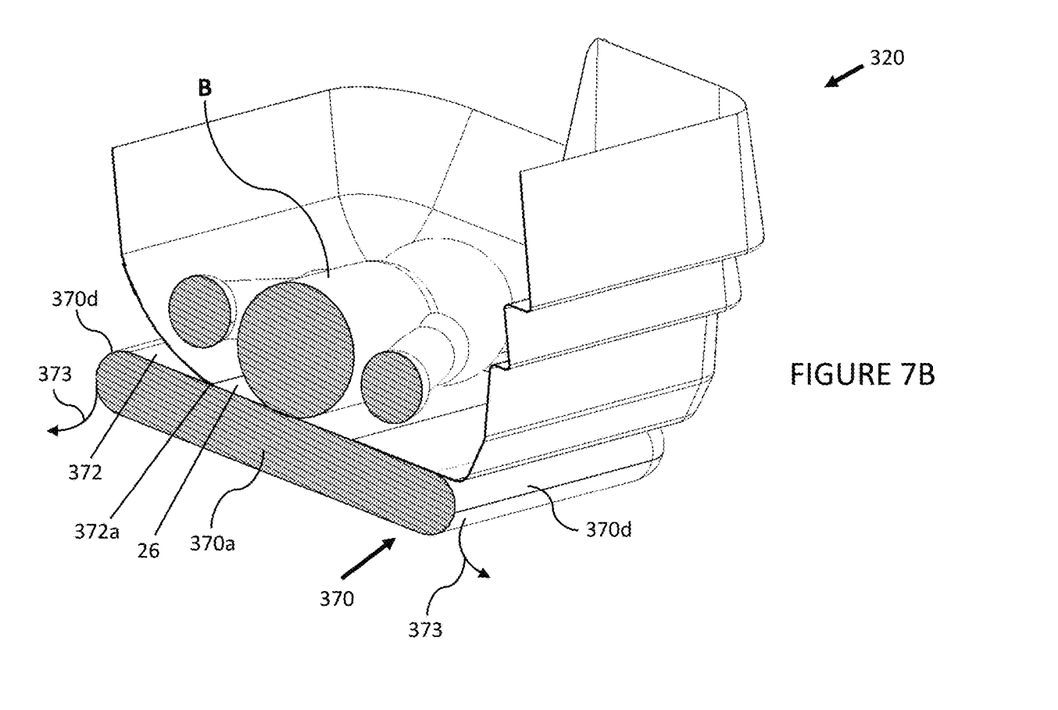
FIG. 7B illustrates a sectioned view of the release door (panel/retainer) of FIG. 7A.

FIGS. 7A and 7B illustrate another example phototherapy device 320. In this example, the bottom 26 of the phototherapy device 320 includes a release door 370. The release door 370 includes a panel 370*a* and one or more releasable retainers 370*d*.

Similar to the release door 270, the release door 370 is configured to facilitate the prevention of the phototherapy device 320 from being used as a carrier. For instance, in the event that the phototherapy device 320 is picked up with the baby B in it, the releasable retainer or retainers 370*d* release under the weight of the baby B such that the panel 370*a* remains substantially in place. Similar to above, the weight under which the panel 370*a* releases is about 1 pound or more. The baby B can thus remain in a substantially unmoved position by in essence "withdrawing" the bottom 26 as the phototherapy device 320 is lifted upwards around the baby B.

In the illustrated example, the releasable retainer 370*d* is a flexible sheet 372, such as but not limited to an elastic sheet (e.g., vinyl) that is affixed at the bottom of the phototherapy device 320. The flexible sheet 372 wraps partially around the panel 370*a*, which in this example is a mattress. The bottom 26 is open such that an upward-facing region or surface of the panel 370*a* is exposed and serves as the support for the baby B. The flexible sheet 372 wraps around the sides of the panel 370*a* to the bottom side or surface of the panel 370*a*. The elasticity of the flexible sheet 372 generally maintains the panel 370*a* in place during use of the phototherapy device 320, although the panel 370*a* may shift somewhat. Upon lifting of the phototherapy device 320, however, the weight of the baby B overcomes the elasticity of the flexible sheet 372 such that the flexible sheet 372 is unable to hold the panel 370*a* in place and thus releases as shown at 373. As a result, the panel 370*a*, and baby B, remain substantially in place as the remainder of the phototherapy device 320 is lifted upwards around the baby B.

Figure 8A:
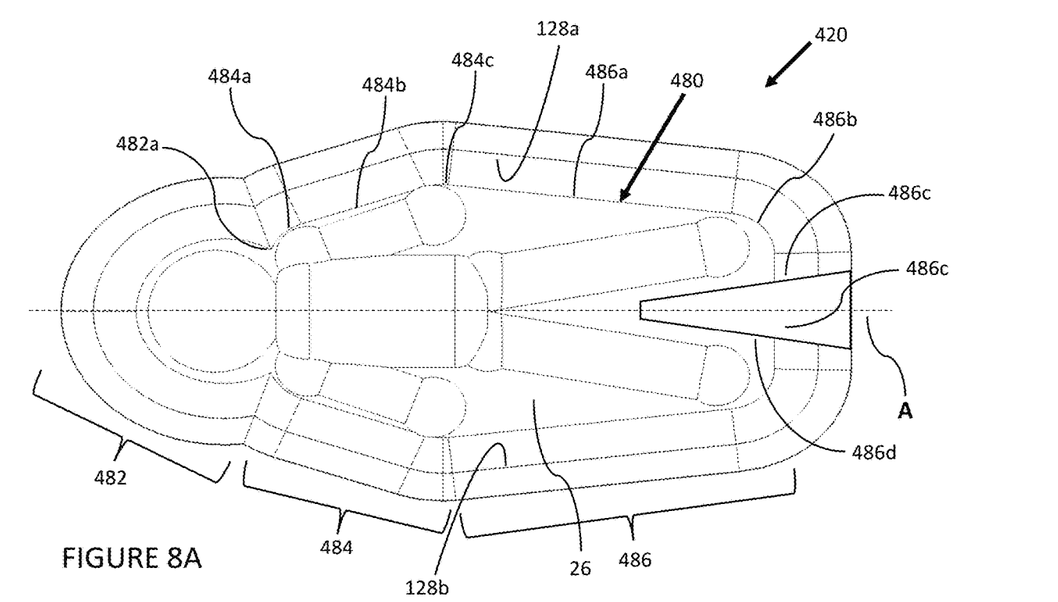
FIG. 8A illustrates an overhead view of a fitted shape phototherapy device.
Figure 8B:
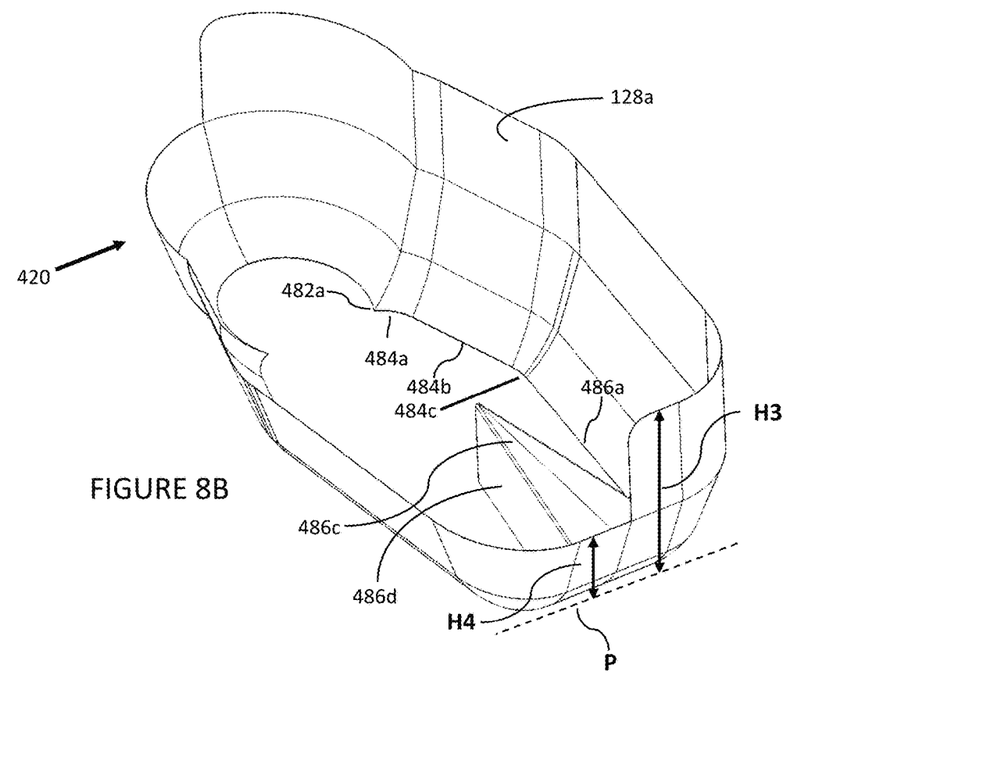
FIG. 8B illustrates an isometric view of the device of FIG. 8A.

FIGS. 8A and 8B illustrate another example of a phototherapy device 420. While the devices of the prior examples have a racetrack oval shape, the phototherapy device 420 defines a fitted shape 480 with respect to human body shape. In other words, the fitted shape 480 generally follows the outline of a human, such as the baby B (when viewed vertically with the baby B lying flat). The fitted shape 480 is generally symmetric about the longitudinal axis A of the phototherapy device 420 and includes a head region 482, a torso region 484, and a leg region 486, that correspond in shape, respectively, to the head, torso, and legs of the baby B. In this regard, the head region 482 is generally circular or pseudo-circular in outline and tapers to a neck 482*a*. The torso region 484 extends from the neck 482*a* and includes a shoulder 484*a*. The shoulder 484*a* has a concave curvature and diverges from the neck 482*a* to an arm section 484*b*. The arm section 484*b* is generally straight and further diverges to a hip point 484*c*. The leg region 486 includes a thigh section 486*a* that extends from the hip point 484*c*. The thigh section 486*a* is generally straight and converges to a foot section 486*b*. The foot section 486*a* converges along a curvature to a wedge section 486*c*. The wedge section 486*c* projects toward the head and torso regions 482/484, but only a relatively short distance that is partially into the thigh section 486*a*. The wedge section 486*c* extends in the space that will be between the legs of the baby B, thereby facilitating maintaining the legs apart for greater light exposure and to help prevent rollover of the baby. Additionally, the wedge section 486*c* includes reflective surfaces 486*d* to further redirect light towards the legs of the baby B. For example, the reflective surfaces 486*d* are specular or diffuse as described herein.

The fitted shape 480 facilitates enhancing efficiency of light transfer to the baby B. For instance, in comparison to the racetrack oval shape, the fitted shape 480 more closely tracks the outline of the baby B, thereby providing a relatively more uniform and shorter distance between the baby B and the reflective surfaces 128*a*/128*b*. A more uniform and shorter distance facilitates reducing light loss and increasing light impingement on the baby B. In particular, the fitted shape 480 may enhance efficiency of light transfer for statistically high and low weight percentile babies.

In additional examples the phototherapy devices disclosed herein include further features to facilitate use and/or effectiveness. It is to be understood that although the following examples may be presented with respect to a particular phototherapy device (e.g., device 120), that the examples are applicable to each one of the disclosed phototherapy devices.

Figure 9:
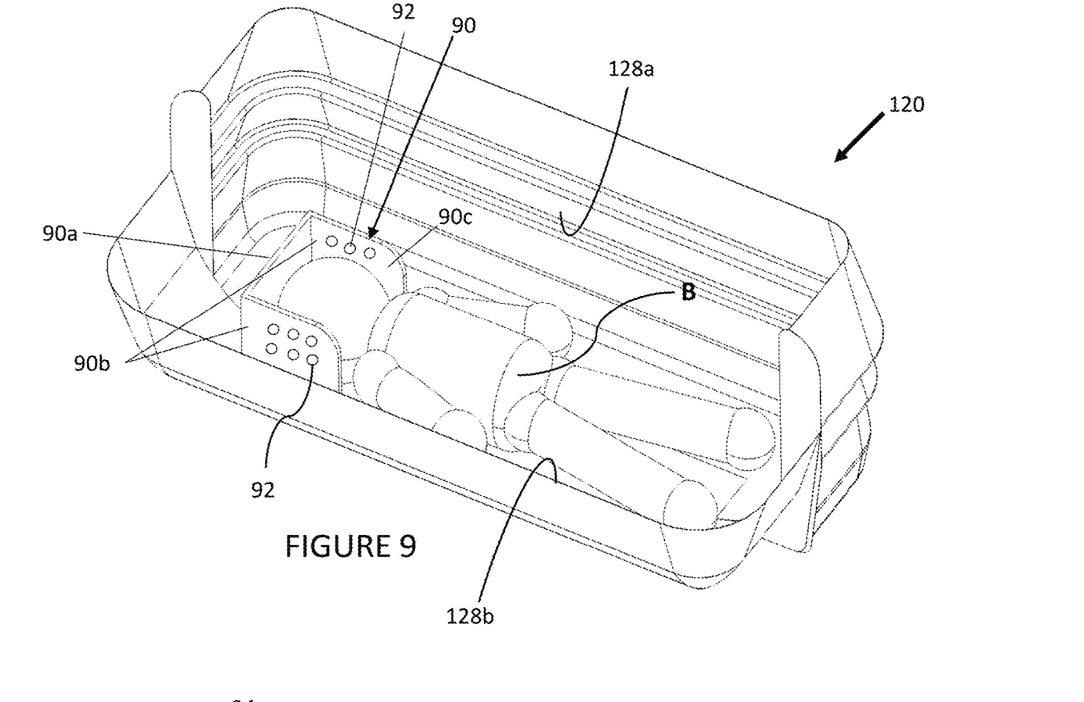
FIG. 9 illustrates an example phototherapy device with a head alignment structure.

As shown in FIG. 9, the illustrated phototherapy device 120 additionally includes a head alignment structure 90. The structure 90 includes a top wall 90*a* and side walls 90*b* that are joined by the top wall 90a. The walls 90a/90b define an interior head pocket 90c in which the head of the baby B resides. The walls 90a/90b and pocket 90c serve to facilitate providing support and/or alignment of the head of the baby B. One or more of the walls 90a/90b are transparent so as to permit the light L to impinge the head region of the baby B. The structure 90 may therefore be used to provide support/alignment, yet minimally block the light L for therapy.

In examples, one or more of the walls 90a/90b are formed of a transparent polymer, such as but not limited to, acrylic, polymethylmethacrylate (PMMA), or polyethyleneterephthalate (PET). In the illustrated example, one or more of the walls 90a/90b have vents 92 that facilitate air exchange around the head of the baby B. For instance, the vents are open passages and/or screened passages (e.g., stainless steel mesh).

Figure 10:
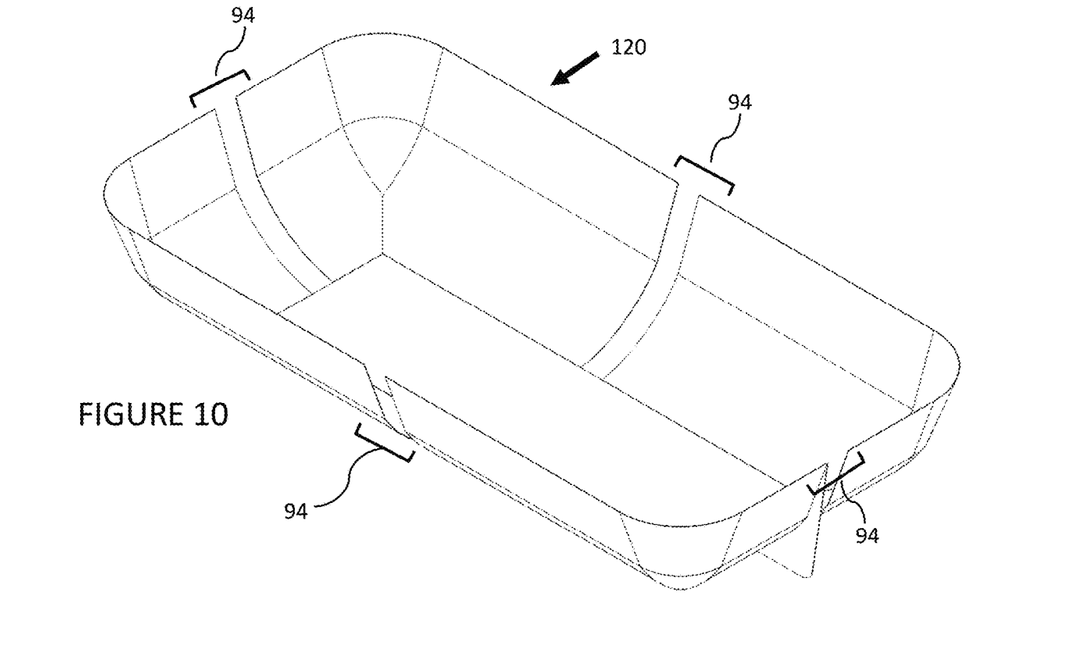
FIG. 10 illustrates another example phototherapy device that is expandable.

As shown in FIG. 10, the phototherapy device 120 additionally includes one or more expanding slits 94 in the device walls. The slits 94 permit a user to adjust the longitudinal and transverse sizes of the phototherapy device 120, such as to better conform to the size of the baby B, or to better conform to different size bassinets.

Figure 11:
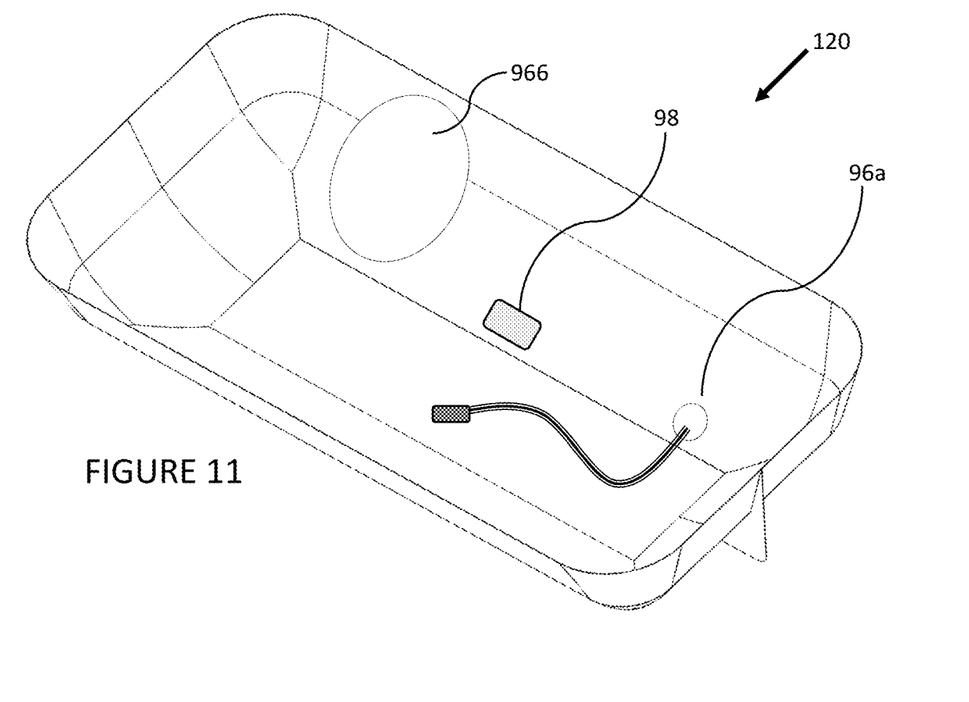
FIG. 11 illustrates another example phototherapy device that has an access port and a window.

As shown in FIG. 11, the phototherapy device 120 additionally includes a port 96a and window 96b. For instance, the port 96a is a passage that connects the interior and exterior of the phototherapy device 120. The port 96a may be used to provide access for cords, tubes, sensors, cameras, or other lines or equipment. The window 96b is transparent and permits a user to see at least a portion of the baby B from a horizontal viewpoint. In this example, the phototherapy device 120 also includes a weight 98. For instance, the weight 98 makes tipping of the device 120 more difficult.

Figure 12:
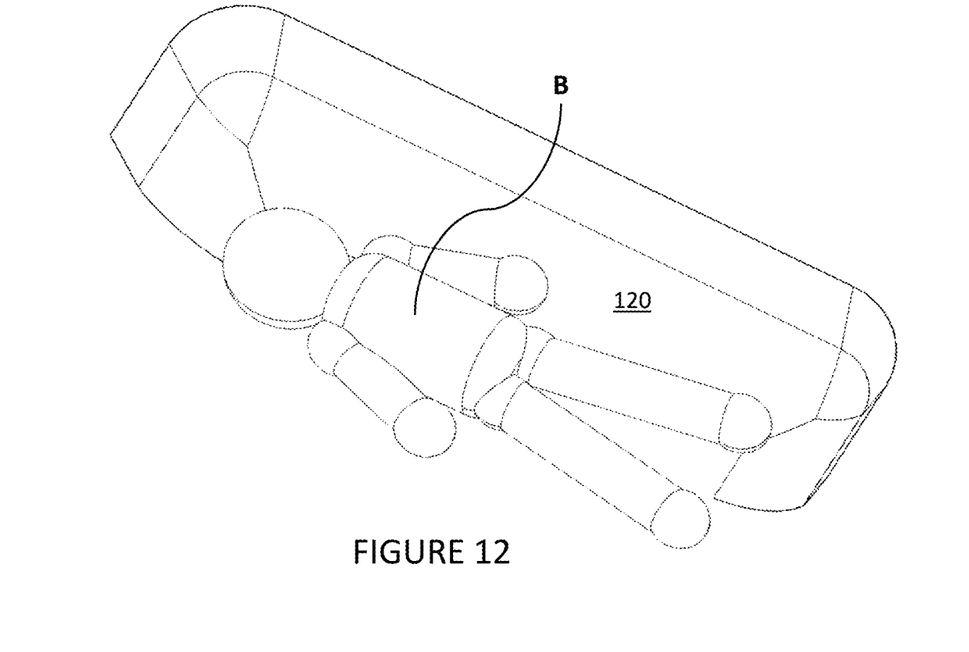
FIG. 12 illustrates a phototherapy ring segment.

FIG. 12 shows a modified version of the phototherapy device 120 in which the device 120 is a ring segment, i.e., a portion of ring that extends only part of the way around the region R. The device 120 therefore illuminates less than 100% of the perimeter of the region R, e.g., less than 100% of the perimeter of the baby. In examples, the ring segment includes the diffuse reflector as described above (e.g., surfaces 28a/128a), the specular reflector as described above (e.g., surfaces 28b/128b), or a combination of diffuse and specular reflector surfaces. In one example, the ring segment is approximately half of the ring 22 as in any of the prior examples, e.g., the front half (with surface 28b/128b) or the back half (with surfaces 28a/128a). The ring 120 may facilitate observation of the baby by a doctor or nurse while still partially providing phototherapy.

Figure 13A:
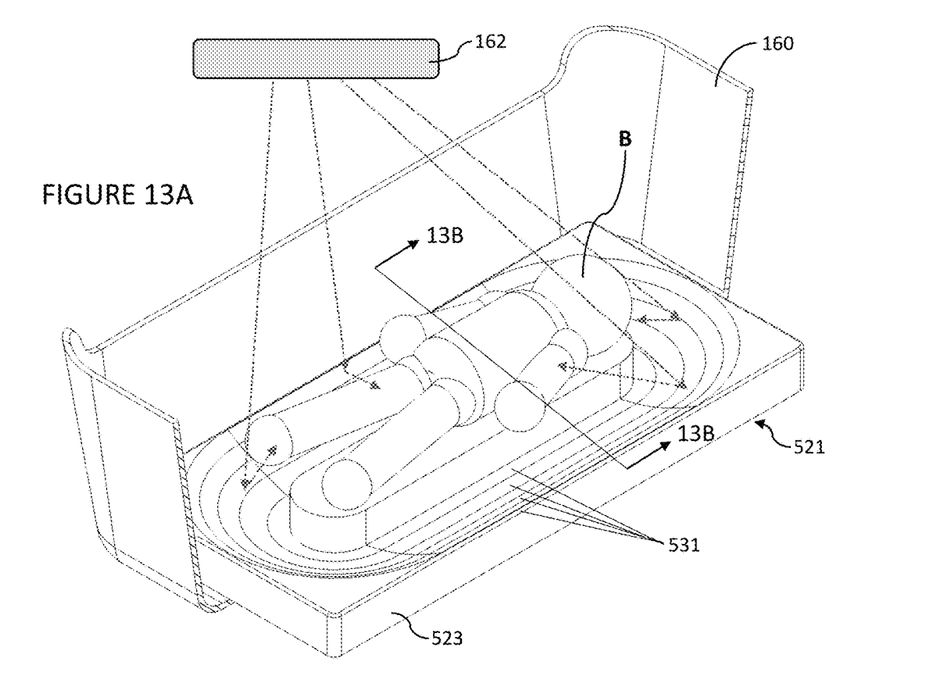
FIG. 13A illustrates a reflective mattress.
Figure 13B:
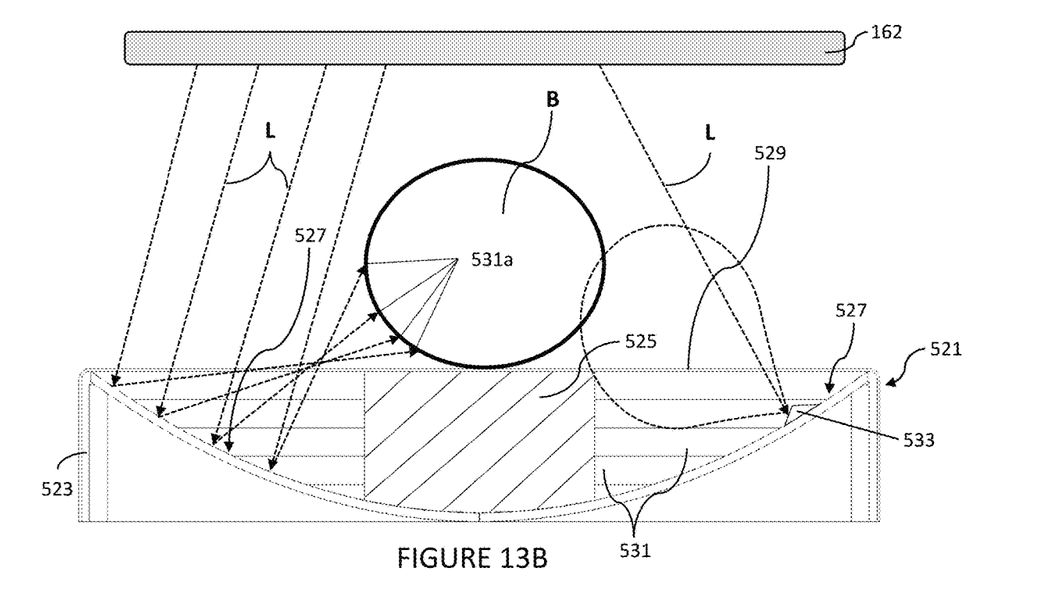
FIG. 13B illustrates a sectioned view of the mattress of FIG. 13A.

FIGS. 13A and 13B illustrate another example phototherapy device 521. In this example, the phototherapy device 521 includes a frame 523 that includes a body support 525, reflective surfaces 527, and support surface 529. The frame 523 is generally rigid and able to support the weight of the surfaces 527/529 and the baby B without substantially deflecting such that its basic shape is lost. For instance, the frame 523 is formed of a polymer, such as but not limited to, acrylonitrile butadiene styrene (ABS), polyphthalamide (PPA), polyphenylene sulfide (PPS), or polyoxymethylene (POM). The reflective surfaces 527 generally form a concave shape relative to the support surface 529. The support surface 529 is transparent and may be formed of clear vinyl, for example. The body support 525 may be formed of foam, such as but not limited to polyester foam or elastic bands. The body support is sandwiched between the frame 521 and the support surface 529.

In the illustrated example, the reflective surfaces 527 are provided by concentric parabolic reflectors 531 and/or angled reflectors 533. For instance, the reflectors 531/533 are specular reflectors, diffuse reflectors, or combinations thereof. The reflectors 531/533 reflect incoming light L from the overhead light source 162 toward the baby B. In one example, there are one or more of the parabolic reflectors 531. Each such parabolic reflector 531 has a focal point 531a. In further examples, the focal points 531a of two or more parabolic reflectors coincide, although in other examples the focal points 531a of two or more parabolic reflectors do not coincide. The focal point or points 531a correspond to the region in which the baby B will lay, which is generally the local region extending upwards from the body support 525.

In some end use environments, the geometry of the structure that holds a phototherapy device, such as a bassinet or an incubator, may not be able to physically accommodate the shape of the prior example phototherapy devices. In that regard, by comparison, the phototherapy device 521 is relatively compact and low-profile yet facilitates redirecting light that would otherwise not impinge the baby B back upwards toward the baby B.

Unfortunately, many known phototherapy systems are highly inefficient in transferring the light to the baby, thereby extending the length of time of treatment and consuming excess electrical power. Due to the curvature of the body, many known phototherapy systems concentrate light along the longitudinal axis of the body, at the surface nearest the light source. Such systems provide poor light distribution to body surfaces that curve away from the incident light or that are out of line-of-sight of the light source. These systems may also consume substantial amounts of electrical power, while actually returning less than 3 percent of that power as light that impinges the baby. The phototherapy devices as disclosed herein are designed to facilitate reducing light loss and thus enhance efficiency and power use.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A phototherapy device comprising:
    a ring having an open top side and side walls that circumscribe a central region for receiving a phototherapy subject, the side walls including a work surface that is configured to receive visible light through the open top side and reflect the visible light toward the central region for phototherapy, the side walls including a front side and a back side opposite the front side across the central region, the work surface on the back side facing forward toward the front side and including a first surface that is a diffuse reflector, and the work surface on the front side facing toward the back side and including a second surface that is a specular reflector.

2. The phototherapy device as recited in claim 1, wherein the specular reflector or the diffuse reflector makes up at least 15% of the surface area of the work surface, and the other of the specular reflector or the diffuse reflector makes up a remainder of the surface area of the work surface.

3. The phototherapy device as recited in claim 1, wherein the specular reflector or the diffuse reflector makes up at least 40% of the surface area of the work surface, and the other of the specular reflector or the diffuse reflector makes up a remainder of the surface area of the work surface.

4. The phototherapy device as recited in claim 1, wherein the ring has a racetrack oval shape and the back side and the front side are two opposed elongated walls that extend approximately parallel to a longitudinal axis.

5. The phototherapy device as recited in claim 1, wherein the diffuse reflector is a Lambertian reflector.

6. The phototherapy device as recited in claim 1, wherein the diffuse reflector has a TAPPI brightness of 70 to 130, and the specular reflector has a reflectance of at least 70% based on a quotient of radiance reflected and radiance received.

7. The phototherapy device as recited in claim 1, wherein the diffuse reflector includes one or more additives that are operable to convert ultraviolet radiation that is received through the open top side into visible light.

8. The phototherapy device as recited in claim 1, wherein the first surface has ridges, each said ridge including a portion that is sloped relative to vertical toward a bottom of the ring.

9. The phototherapy device as recited in claim 8, wherein the bottom is reflective.

10. The phototherapy device as recited in claim 1, wherein a portion of the side wall that has the specular reflector has a height H1 taken from a horizontal plane of a bottom of the ring and another portion of the side wall that has the diffuse reflector has a height H2 taken from the horizontal plane, and the height H1 is 20% to 80% of the height H2.

11. The phototherapy device as recited in claim 1, wherein the ring includes a bottom, and the bottom has a release door.

12. The phototherapy device as recited in claim 11, wherein the release door includes a panel and a hinge.

13. The phototherapy device as recited in claim 11, wherein the release door includes a panel and an elastic retainer.

14. The phototherapy device as recited in claim 1, wherein the ring has a fitted shape with respect to human body shape.

15. The phototherapy device as recited in claim 1, further comprising a head alignment structure that defines an interior head pocket and vents.

16. A phototherapy system comprising:
a light source operable to emit visible light; and
a ring vertically below the light source, the ring having an open top side and side walls that circumscribe a central region for receiving a phototherapy subject, the side walls including a work surface that is configured to receive the visible light through the open top side and reflect the visible light toward the central region for phototherapy, the side walls including a front side and a back side opposite the front side across the central region, the work surface on the back side facing forward toward the front side and including a first surface that is a diffuse reflector, and the work surface on the front side facing aft toward the back side and including a second surface that is a specular reflector.

17. The phototherapy device as recited in claim 16, wherein the ring includes a front and a back, the light source obstructs the back, the diffuse reflector is on the back, and the specular reflector is on the front.

18. The phototherapy device as recited in claim 1, wherein the work surface on the back side excludes any spectral specular reflectors.

19. The phototherapy device as recited in claim 1, wherein the second surface that is the specular reflector includes a parabolic portion having multiple focal points.

20. A phototherapy device comprising:
a ring having an open top side and side walls that circumscribe a central region for receiving a phototherapy subject, the side walls including a work surface that is configured to receive visible light through the open top side and reflect the visible light toward the central region for phototherapy, the work surface including a first surface that is a diffuse reflector and a second surface that is a specular reflector, the second surface that is the specular reflector including a parabolic portion having multiple focal points in the central region.

\* \* \* \* \*

UNITED STATES PATENT AND TRADEMARK OFFICE
CERTIFICATE OF CORRECTION

| | |
|---|---|
| PATENT NO. | : 11,497,930 B2 |
| APPLICATION NO. | : 16/696197 |
| DATED | : November 15, 2022 |
| INVENTOR(S) | : Patrick Kenneth Powell |

It is certified that error appears in the above-identified patent and that said Letters Patent is hereby corrected as shown below:

In the Specification

Column 1, Line 17, insert the following:
--STATEMENT REGARDING FEDERALLY SPONSORED SUPPORT
This invention was made with government support under R41 HD093478 awarded by the National Institutes of Health (NIH). The government has certain rights in the invention.--

Signed and Sealed this
Seventh Day of March, 2023

Katherine Kelly Vidal
*Director of the United States Patent and Trademark Office*